United States Patent [19]

Deppert et al.

[11] Patent Number: 5,211,942
[45] Date of Patent: May 18, 1993

[54] HALIDE CONTAINING QUATERNARY AMMONIUM SALTS AS HAIR CONDITIONING AGENTS

[75] Inventors: Thomas M. Deppert, Waterbury; Janusz Z. Jachowicz, Bethel, both of Conn.

[73] Assignee: Clairol Incorporated, New York, N.Y.

[21] Appl. No.: 719,883

[22] Filed: Jun. 21, 1991

Related U.S. Application Data

[62] Division of Ser. No. 562,306, Aug. 3, 1990, Pat. No. 5,030,756.

[51] Int. Cl.$^5$ .............................................. A61K 7/075
[52] U.S. Cl. ....................................... 424/70; 132/202
[58] Field of Search ............................ 424/70, 71, 47; 132/202; 564/291

[56] References Cited

U.S. PATENT DOCUMENTS 4,960,588 10/1990 Hoshowski et al. ................. 424/47
5,034,219 7/1991 Deshpande et al. ................. 424/71

Primary Examiner—Thurman K. Page
Assistant Examiner—D. Colucci
Attorney, Agent, or Firm—Charles J. Zeller

[57] ABSTRACT

Processes for conditioning human hair by treatment with selected quaternary ammonium halides, compositions useful for such processes and novel quaternary halides useful in the processes.

6 Claims, No Drawings

HALIDE CONTAINING QUATERNARY AMMONIUM SALTS AS HAIR CONDITIONING AGENTS

This is a divisional application of U.S. Ser. No. 07/562,306 filed Aug. 3, 1990, now U.S. Pat. No. 5,030,756 granted Jul. 9, 1991.

FIELD OF THE INVENTION

This invention is in the field of human hair conditioners to make the hair more manageable.

The invention relates to a process for conditioning human hair especially, although not necessarily after waving, and to compositions, some of the which contain novel compounds, useful for such processes. More particularly, it relates to certain quaternary halides with at least one long chain substituent attached to the nitrogen of the quaternary center. Some of these compounds are novel.

BACKGROUND OF THE INVENTION

It is known that when certain long chain alkyl quaternary ammonium salts are deposited on human hair, they improve combability i.e. the relative ease with which hair can be combed by imparting a certain lubricity to the hair as well as by providing an antistatic effect. Both of these effects combine to make the hair easier to manage so that the desired appearance of the hair can be more readily achieved. Compositions having these properties are called "hair conditioners". See, for example, A.C. Lunn and R.E. Evans, *The Electrostatic Properties of Human Hair*, J. Soc. Cosmet. Chem., 28, 549 (1977).

These hair conditioners appear to function because they are cationic and are easily adsorbed on the anionic surface of human hair. However the conditioning effect is usually short lived because the conditioners wash out of the hair and are substantially eliminated after only a few washings.

The art has made many efforts to overcome the problem and provide durable hair conditioners which will stay in the hair despite repeated washings.

Hannen et al in U.S. Pat. No. 4,299,817 describe an aqueous composition for setting hair which contains as the active ingredient, a polyelectrolyte complex which is the ionic reaction product of one or more polycationic polymers and one or more polyanionic polymers.

Quaternary ammonium salts are also known for other purposes.

For example, U.S. Pat. No. 3,510,248 to Thielan et al discloses certain chloro quanternary compounds for softening cellulosic materials such as cotton textile fibers.

Matter et al in U.S. Pat. No. 3,844,867 describe the use cationic quaternary ammonium halides substituted with an alkylene halide group or an alkyl halide group substituted with a phenylene group for improving the affinity of anionic dyes to textiles such as nylon.

Despite major efforts, however, the art has not yet provided durable hair conditioners which will continue their desired effects in human hair through several shampoos.

THE INVENTION

It has now been discovered that certain mono and dihalo substituted, cationic, quaternary ammonum salts can be employed as hair conditioners which will continue to provide their beneficial conditioning effects through eight or more shampoos. This invention is concerned with such compounds, hair conditioning compositions containing one or more of these compounds and methods of employing them to improve the combability of hair.

The monohalo compounds useful in this invention may be represented by the formulas:

$$CH_3(CH_2)_nCH_2 \underset{Alk}{\overset{+}{\underset{Alk}{N}}} (CH_2)_mX \quad Y^-$$

$$CH_3(CH_2)_nCH_2 \underset{Alk}{\overset{+}{\underset{Alk}{N}}} CH_2CH_2O[CH_2CH_2O]_qCH_2CH_2X \quad Y^-$$

wherein:

X is bromine, chlorine or iodine,

Y is an anion,

Alk is an alkyl group containing from about 1 to about 4 carbon atoms, n is an integer with a value of from about 10 to about 22, m is an integer with a value of from about 1 to about 4 with the proviso that the total number of carbon atoms in the cation is not greater than about 28, and q is an integer with a value from about 0 to about 20 and further compounds in which the long chain alkyl group is interrupted with a phenylene group so that the structure of the interrupted group can be represented by $$CH_3(CH_2)_sCH_2-\!\!\!\left\langle\!\!\!\begin{array}{c}\\ \\ \end{array}\!\!\!\right\rangle\!\!\!-(CH_2)_t-$$

wherein s is an integer of from about 8 to about 17 and t is an integer from about 1 to about 5.

The novel dihalo compounds useful in this invention may be represented by the formulas:

$$CH_3(CH_2)_nCH_2 \underset{Alk}{\overset{+}{\underset{(CH_2)_mX}{N}}} (CH_2)_mX \quad Y^-$$

$$\underset{Alk}{\overset{Alk}{\underset{CH_2(CH_2)_pCH_2X}{\overset{+}{N}}}} CH_2(CH_2)_oCH_2X \quad Y^-$$

wherein

X is bromine, chlorine or iodine

Y is an anion

Alk is an alkyl group containing from about 1 to about 4 carbon atoms n is an integer with a value of from about 10 to about 22 m is an integer with a value of from about 1 to about 4 o is an integer with a value of from about 8 to about 11 p is an integer with a value of from about 8 to about 11, with the proviso that the total number of carbon atoms in the cation is not more than about 28, and further compounds in which one or both long chain alkyl group is interrupted with a phenylene group so that the structure of the interrupted group can be represented by

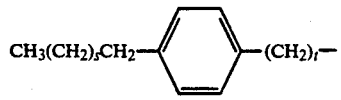

wherein s is an integer of from about 8 to about 17 and t is an integer from about 1 to about 5.

In the preferred compounds of this invention, X is bromine or chlorine and Y$^-$ is a chloride, bromide or iodide.

The compounds of the invention can be prepared by any of number of procedures known to those skilled in the art which are applicable to the preparation of quaternary ammonium compounds and alkyl halides.

For example, an appropriate substituted tertiary amine can be reacted with an $\alpha$, $\omega$- dihaloalkane as described in U.S. Pat. Nos. 3,557,214 and 3,987,097 and in the Journal of the American Chemical Society 72,5135 (1950). The compound 1, 2-dibromoethane may be reacted with dimethyl hexadecylamine in an appropriate nonpolar solvent such as benzene or hexane at about 60° C. External cooling may be necessary to control the reaction. The quaternary salt, dimethyl- (2-bromoethyl)-hexadecyl ammonium bromide settles out as it forms. This procedure is not applicable to the preparation of dihalo compounds.

The presently preferred procedure for preparing the monobromo and novel dibromo compounds of the invention is to react the corresponding alcohols, all of which are known or can be prepared by known methods with phosporous tribromide, phosphorous oxybromide or thionyl bromide. Of these, phosphorous tribromide is preferred because it affords good yields and is relatively easy to work with.

Reaction is effected at ambient temperature, i.e. about 20° to about 40° C. over a period of from about 10 to about 16 hours in a reaction inert, organic, nonpolar, aliphatic or aromatic hydrocarbon solvent containing up to about eight carbon atoms such as benzene, toluene, hexane or octane. A small molar excess of the tribromide is employed to assure as complete a reaction as possible.

For the preparation of the chlorides, the corresponding alcohol is reacted with analogous chlorine containing compounds such as phosphorous oxychloride or thionyl chloride. In these instances, the latter reactant is preferred because it affords good yields and the unwanted by-products are easily removed as vapors. Additionally, it can serve as a solvent for the reaction.

The reaction is carried at ambient temperature during a period of from about 24 to about 72 hours.

Both types of reactions may be carried out in the presence of an acid scavenger, such as pyridine. The scavenger should, of course, be reaction inert except for its ability to react with product hydrogen bromide or hydrogen chloride which form as by products.

The following non-limiting examples illustrate these methods of preparing compounds of the invention.

EXAMPLE 1

DIMETHYL-(2-BROMOETHYL)-HEXADECYL AMMONIUM BROMIDE

A total of 3.95g (0.010 mole) of dimethyl-(2-hydroxy)ethyl-hexadecyl ammonium bromide and 0.9910g (0.00366 mol phosphorous tribromide was slurried in 20 ml of benzene and allowed to react at room temperature (about 25° C.) with stirring for 24 hours under nitrogen. The solvent was removed in vacuo and the residue washed several times with anhydrous ether. The resulting amorphous solid was recrystallized from ethyl acetate, filtered and dried to yield 3.57g (77%) of the desired product. Calc. % C 52.51, % H 9.49, %N 3.06, %Br 34.93; Found % C 51.80, H 10.06, %N 3.06, % Br 34.18; m.p. 185°–190° C. The $^1$H NMR and IR agree with the proposed structure.

EXAMPLE 2

DIMETHYL-(2-CHLOROETHYL)-HEXADECYL AMMONIUM BROMIDE

A total of 3.95g (0.0100 mole) of dimethyl-2 (hydroxyethyl) hexadecyl ammonium bromide was slurried in 20 ml of thionyl chloride as both reactant and solvent. Crosslinked polyvinylpyridine (1.05g, 0.010 mole) was added as an HCl scavenger and the mixture allowed to react at about 25° C. with stirring for 48 hours. The scavenger was removed by filtration, and the solvent removed in vacuo. The residue was recrystallized from acetonitrile, filtered and dried to afford 2.73g (66%) of the desired compound.

Calc (as a Br$^-$salt) % C 58.16, % H 10.52, %N 3.39

Calc. (as a Cl$^-$salt) % C 65.18, % H 11.78, % N 3.80; Found % C 58.37, % H 10.86, % N 3.33. These FIGURES establish that the compound formed is the desired bromide salt.

Utilizing these procedures, the compounds listed below were prepared. They were all identified by elemental analysis, $^1$H NMR and IR. They are all novel and are the presently preferred compounds of the invention.

Methyl -di [(2-bromoethyl)]-hexadecyl ammonium bromide.

Dimethyl -di [(11- bromoundecyl)]-ammonium bromide

Dimethyl -2-(bromoethyl) - 4-(dodecyl)phenylmethylene ammonium bromide

Dimethyl - hexadecyl -[2-(bromoethoxy)ethyl]ammonium bromide.

The compounds listed in Table I are all prepared as described above and are useful in the practice of this invention.

TABLE I $$R_2 \overset{R_1}{\underset{R_3}{\overset{+}{-}N-}} R_4 \quad Y^-$$

| R$_1$ | R$_2$ | R$_3$ | R$_4$ | Y |
|---|---|---|---|---|
| CH$_3$ | CH$_3$ | CH$_3$(CH$_2$)$_{14}$CH$_2$ | CH$_2$CH$_2$Cl | Cl |
| CH$_3$ | CH$_3$ | CH$_3$(CH$_2$)$_{14}$CH$_2$ | CH$_2$CH$_2$Br | Cl |
| CH$_3$ | CH$_3$ | CH$_3$(CH$_2$)$_{14}$CH$_2$ | (CH$_2$)$_3$Br | Br |
| CH$_3$ | CH$_3$ | CH$_3$(CH$_2$)$_{14}$CH$_2$ | (CH$_2$)$_3$Cl | Br |
| CH$_3$CH$_2$ | CH$_3$ | CH$_3$(CH$_2$)$_{12}$CH$_2$ | CH$_2$CH$_2$Br | Br |
| CH$_3$CH$_2$ | CH$_3$ | CH$_3$(CH$_2$)$_{10}$CH$_2$ | CH$_2$CH$_2$Cl | Br |
| CH$_3$CH$_2$ | CH$_3$ | CH$_3$(CH$_2$)$_{10}$CH$_2$ | CH$_2$CH$_2$Br | Br |
| CH$_3$CH$_2$ | CH$_3$ | CH$_3$(CH$_2$)$_{18}$CH$_2$ | CH$_2$CH$_2$Br | Br |

TABLE I-continued $$R_2 \overset{R_1}{\underset{R_3}{\overset{+}{-}N-R_4}} \quad Y^-$$

| R₁ | R₂ | R₃ | R₄ | Y |
|---|---|---|---|---|
| CH₂CH₂Br | CH₃ | CH₃(CH₂)₁₁CH₂ | CH₂CH₂Br | Br |
| CH₂CH₂Br | CH₃CH₂ | CH₃(CH₂)₁₀CH₂ | CH₂CH₂Br | Br |
| CH₂CH₂Cl | CH₃(CH₂)₃ | CH₃(CH₂)₁₂CH₂ | CH₂CH₂Cl | Br |
| CH₂CH₂Cl | CH₃CH₂ | CH₃(CH₂)₁₄CH₂ | CH₂CH₂Cl | Cl |

The hair conditioning agents of this invention have a number of advantages compared to hair conditioners of the prior art. Their principal advantage is that they are very durable and will remain in the hair as effective conditioners even after several shampoos, e.g. four to eight or more. Their durability is attributable to at least two factors. One is that they form ionic bonds with the hair. The other is that they form covalent bonds with the hair.

As is known, the keratin in human hair carries an anionic charge. The hair conditioners of the invention are cationic and are electrostatically attracted and bound to the hair. Human hair, especially after waving with reducing agents such as thioglycolic acid has a number of free mercaptan groups formed by reductive cleavage of the disulfide bonds of cystine. The compounds of this invention react with the free mercaptan groups to form covalent bonds which bind the conditioner to the hair. The presence of the long chain alkyl group in the moiety chemically joined to the hair improves the lubricity. As a result of these two reactions, the combability of the hair is improved.

The reaction for the formation of covalent bonds is illustrated below wherein R represents the long chain substituent and K represents heratin protein.

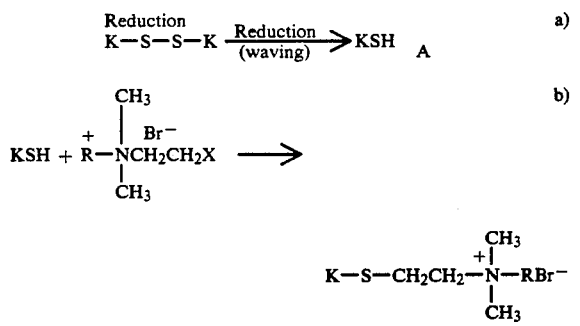

The dihalo hair conditioners of the invention are preferred because, as will be apparent from their structure, each molecule is capable of forming two covalent bonds with the sulfhydryl radicals of the hair.

The products of this invention are especially useful after a reduction (waving) with a thioglycolate such as ammonium thioglycolat or with an inorganic reducing agent such as sodium bisulfite However, they may also be employed with untreated or virgin hair, dye hair, relaxed hair and bleached hair In all cases they reduce the combing work as determined by the method of Garcia and Diaz described in J. Soc. Cosmet. Chem. 27, 379-398 (Sep. 1976).

Combability can be defined as the subjective perception of the relative ease or difficulty with which human hair can be combed. It depends on the magnitude and the fluctuations of the forces that oppose combing.

As discussed at page 379 by Garcia and Diaz in the cited publication which is incorporated herein by reference:

Combability is an important attribute, which is always considered when judging the "condition" of human hair. Improved combability is perceived as the hair being in better condition. Another concept closely associated with combability is that of manageability. Still another factor related to combability is that of the mechanical damage, which is done to hair with the combing process, which is accelerated if the hair is hard to comb or to untangle. It follows that combability, due to its close connection with other desirable hair qualities, is a very important factor in judging the performance of many hair care products.

The hair conditioners of this invention will normally be contacted with the hair to be treated from water or water/alcohol solutions containing from about 0 1% to about 10% by weight, based on the total weight of the composition, of at least one of the active agents. Preferred solutions will contain from about 0.5% to 5% of at least one conditioner. Aqueous solutions are preferred, but the compositions may contain up to about 30% by weight of water miscible alkanol, preferably ethanol, isopropanol or benzyl alcohol to assist in solubilizing the conditioner or other components of the composition which may be present. These additional excipients include, for example coloring agents, fragrances, surfactants, buffers, preservatives, viscosity enhancers, gelling agents, silicones or other emulsifying agents, and other common adjucents well known to those skilled in the art.

The compositions may be provided as foams, gels, aerosols or other standard forms normally employed with such products. These may be produced by procedures will known to the skilled artisan They are generally utilized in the same manner as other hair conditioning compositions The contact time is from about 5 to about 30 minutes.

A number of tests have been conducted with the conditioners of this invention to determine their efficacy as hair conditioning agents. These test were conducted on untreated, reduced and dyed hair at various pH values The results are shown in Table II.

For untreated hair, each experiment was performed on a 6 inch 2g tress of untreated brown hair. Measurements of wet combing work were obtained on an Instron Model 1110 with a cross-head speed of 10 cm/min using the procedure cited above. The results reported in the table are the average of the measurements obtained for two tresses.

The conditioners tested were:

A: Dimethyl - (2-bromoethyl)-hexadecyl ammonium bromide, and

B: Methyl - di - [(2- bromoethyl)]- hexadecyl ammonium bromide.

In the first set of tests on untreated hair, the hair was treated with a 1% aqueous solution of the selected conditioner for 30 minutes at room temperature and then rinsed with warm tap water for 1 minute In the subsequent shampooing, the hair was lathered with 0.5g of a commercial shampoo for 30 seconds followed by rinsing under warm tap water for 30 seconds.

For reduction, the hair was treated with ammonium thioglycolate (6% adjusted to pH 9) for 10 minutes at room temperature and rinsed with tap water for 1 minute. Then it was treated with 10 ml of an aqueous 1% solution of the selected conditioner for 30 minutes at room temperature prior to neutralization, i.e. oxidation with 10 ml. of 3% $H_2O_2$ for 8 minutes at room temperature. It was then shampooed as described above.

The tests were extended to dyed hair. After dyeing with a commercial oxidation dye, the hair was treated with 10 ml of a 1% aqueous solution of the selected conditioner for 30 minutes at room temperature and then rinsed with tap water for one minute. Shampooing was performed as described above.

The results are shown in Table II below:

TABLE II

| Treatment | pH of the Treatment | Wet Combing Work (g*cm) | | |
|---|---|---|---|---|
| | | After Treatment | After 4 Shampoos | After 8 Shampoos |
| Without Reduction | | | | |
| Untreated (Virgin) | 5.3 | 952 | 3006 | 2941 |
| | 10.7 | 1114 | 1855 | 3270 |
| Conditioner A | 5.3 | 688 | 986 | 1878 |
| | 10.7 | 1222 | 1068 | 1542 |
| Conditioner B | 5.3 | 785 | 846 | 1744 |
| | 10.7 | 1038 | 553 | 2384 |
| With Reduction | | | | |
| Untreated (Reduced) | 5.3 | 1515 | 3470 | 3846 |
| | 10.7 | 1005 | 3625 | 4262 |
| Conditioner A | 5.3 | 4036 | 1155 | 1538 |
| | 10.7 | 4524 | 751 | 1474 |
| Conditioner B | 5.3 | 3355 | 1165 | 2781 |
| | 10.7 | 3911 | 2315 | 3176 |
| Untreated (Dyed) | 10.7 | 5956 | 5721 | 4439 |
| Conditioner A | 10.7 | 2952 | 3982 | 3356 |
| Conditioner B | 10.7 | 2888 | 3182 | 3825 |

It will be seen that the use of the products of the invention results in improved combability and that they are effective over a wide pH range.

The work was further expanded (see Table III) to include the effect of concentration on the durability of the surfactants. For reduction, the hair was treated with 10 ml of ammonium thioglycolate (10% adjusted pH 9.2) for 30 minutes at room temperature and rinsed with warm tap water for 1 minute. Then it was treated with 10 ml of an aqueous 5% solution of the selected conditioner for 5 or 30 minutes with room temperature prior to neutralization as described above. Subsequent shampooings were performed as described above.

TABLE III

| | Wet Combing Work (g*cm) | | | |
|---|---|---|---|---|
| 30 min. Treatments | After Treatment | After 4 Shampoos | After 8 Shampoos | Liquid Retention (%) |
| Untreated (reduced only) | 833 | 2805 | 3136 | 40 |
| 5% Stearalkonium Chloride | 385 | 534 | 2287 | 41 |
| 5% Conditioner A | 1075 | 435 | 1549 | 34 |
| 5% Conditioner B | 689 | 415 | 697 | 36 |
| 5 min. Treatments | After Treatment | After 4 Shampoos | | |
| Untreated (reduced only) | 833 | 2805 | | |
| 5% Stearalkonium Chloride | 500 | 628 | | |
| 5% Conditioner A | 1416 | 460 | | |
| 5% Conditioner B | 1600 | 1070 | | |

Conclusions based on Table II and Table III.

The results presented in Table II for treatment on hair without reduction shows that the deposition of the conditioners from both high and low pH solutions produces a durable conditioning effect. Without reduction, treatments with conditioner A or B at pH 10.7 produced wet combing work values that were relatively high before shampooing possibly due to a slight overcoating with the conditioner. This effect was even more pronounced in the case of hair treated with conditioner B at pH 10.7. On reduced hair, treatments with conditioner A or B at either pH initially produced wet combing work values that were also relatively high possibly due to a slight overcoating with the conditioner. This effect was even more pronounced in the case of treatments with conditioner A at pH 10.7. As expected in the case of oxidative dyes, both conditioners A and B have a very small effect on the wet combing work. This is due to the lack of reactive —SH groups on the surface of the fiber Further evidence is presented in Table III. When compared to the commercial conditioner stearalkonium chloride both conditioners A and B were effective with conditioner B (the dibromide) being especially durable The five minute treatments show that both conditioners are durable through 4 shampooings with conditioner A having the greatest effect.

The liquid retention of untreated hair is about 35% while for reduced and bleached hair the liquid retention increases to 40–46% depending on the pH of the treatment The incorporation of surfactants containing hydrophobic groups should reduce the liquid retention of the fiber The data demonstrate that conditioners A and B are effective in reducing the liquid retention of reduced hair.

The following non-limiting examples illustrate a variety of compositions within the scope of this invention. Conditioners A and B are the same conditioners identified by chemical name in the foregoing description.

EXAMPLE 3

| Ingredient | Percent |
|---|---|
| Water | 87.055 |
| Acetamide MEA | 3.000 |
| Hydrolyzed Animal Collagen | 0.700 |
| Glycol Stearate | 3.000 |
| Cetyl Alcohol | 1.300 |
| Conditioner A | 2.000 |
| Hydroxyethylcellulose | 0.850 |
| Polysorbate 20 | 1.000 |
| Hydrolyzed Keratin | 0.100 |
| Fragrance | 0.500 |
| Preservatives and Dyes | 0.495 |
| | 100.000 |

EXAMPLE 4

| Ingredient | Percent |
|---|---|
| Water | 87.055 |
| Acetamide MEA | 3.000 |
| Hydrolyzed Animal Collagen | 0.700 |
| Glycol Stearate | 3.000 |
| Cetyl Alcohol | 1.300 |
| Conditioner B | 2.000 |
| Hydroxyethylcellulose | 0.850 |
| Polysorbate 20 | 1.000 |
| Hydrolyzed Keratin | 0.100 |
| Fragrance | 0.500 |
| Preservatives and Dyes | 0.495 |
| | 100.000 |

EXAMPLE 5

| Ingredient | Percent |
| --- | --- |
| Water | q.S. |
| Conditioner A | 3.500 |
| Benzyl Alcohol | 3.000 |
| Cetyl Alcohol | 0.500 |
| Hydroxyethylcellulose | 1.000 |
| Fragrance | 0.500 |
| Preservatives and Dyes | 0.500 |
| Sodium Citrate | 0.015–0.020 |
| Citric Acid | 0.015–0.020 |
| | 100.000 |

EXAMPLE 6

| Ingredient | Percent |
| --- | --- |
| Water | q.S. |
| Conditioner B | 3.500 |
| Benzyl Alcohol | 3.000 |
| Cetyl Alcohol | 0.500 |
| Hydroxyethylcellulose | 1.000 |
| Fragrance | 0.500 |
| Preservatives and Dyes | 0.500 |
| Sodium Citrate | 0.015–0.020 |
| Citric Acid | 0.015–0.020 |
| | 100.000 |

Sodium citrate and citric acid are added to maintain buffer pH 5.0.

What is claimed is:

1. Aqueous compositions useful as hair conditioners for human hair containing from about 0.1 to about 10% by weight of the total composition of at least one compound represented by the formulas;

$$CH_3(CH_2)_nCH_2 \underset{Alk}{\overset{(CH_2)_mX}{\underset{\diagdown}{\overset{\diagup}{N^+}}}} \underset{(CH_2)_mX}{\overset{Y^-}{\diagdown}}$$

$$Alk \underset{Alk}{\overset{CH_2(CH_2)_oCH_2X}{\underset{\diagdown}{\overset{\diagup}{N^+}}}} Y^-$$

wherein:
X is bromine, chlorine or iodine
Y is an anion
Alk is an alkyl group containing from about 1 to about 4 carbon atoms
n is an integer with a value of from about 10 to about 22
m is an integer with a value of from about 1 to about 4
o is an integer with a value of from about 9 to about 11,
with the proviso that the total number of aliphatic carbon atoms in the cation is not more than about 28, and further compounds in which one or both long chain alkyl groups is interrupted with a phenylene group so that the structure of the interrupted group can be represented by $$CH_3(CH_2)_sCH_2 - \underset{}{\bigcirc} - (CH_2)_t -$$

wherein s is an integer of from about 8 to about 17 and t is an integer from about 1 to about 5.

2. Aqueous compositions useful as hair conditioners for human hair containing from about 0.1 to about 10% by weight of the composition of at least one compound represented by the formulas:

$$CH_3(CH_2)_nCH_2 \underset{Alk}{\overset{(CH_2)_mX}{\underset{\diagdown}{\overset{\diagup}{N^+}}}} Y^-$$

$$CH_3(CH_2)_nCH_2 \underset{Alk}{\overset{CH_2CH_2O[CH_2CH_2O]_qCH_2CH_2X}{\underset{\diagdown}{\overset{\diagup}{N^+}}}} Y^-$$

$$CH_3(CH_2)_nCH_2 \underset{Alk}{\overset{(CH_2)_mX}{\underset{\diagdown}{\overset{\diagup}{N^+}}}} Y^-$$

$$CH_3(CH_2)_nCH_2 \underset{Alk}{\overset{CH_2CH_2O[CH_2CH_2O]_qCH_2CH_2X}{\underset{\diagdown}{\overset{\diagup}{N^+}}}} Y^-$$

X is bromine, chlorine or iodine,
Y is an anion,
Alk is an alkyl group containing from about 1 to about 4 carbons,
n is an integer with a value of from about 10 to about 22, and
m is an integer with a value of from about 1 to about 4 with the proviso that the total number of aliphatic carbon atoms in the cation is not greater than about 28, and
q is an integer with a value of from about 0 to about 20 and further compounds in which one or both long chain alkyl group are interrupted with a phenylene group so that the structure of the interrupted group can be represented by $$CH_3(CH_2)_sCH_2 - \underset{}{\bigcirc} - (CH_2)_t -$$

wherein s is an integer of from about 8 to about 17 and t is an integer from about 1 to about 5.

3. A process for conditioning human hair which comprises treating the hair with an aqueous composition containing from about 0.1 about 10% by weight of the total composition of at least one compound represented by the formulas $$CH_3(CH_2)_nCH_2 \underset{Alk}{\overset{(CH_2)_mX}{\underset{\diagdown}{\overset{\diagup}{N^+}}}} \underset{(CH_2)_mX}{\overset{Y^-}{\diagdown}}$$

-continued

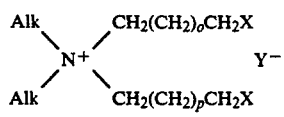

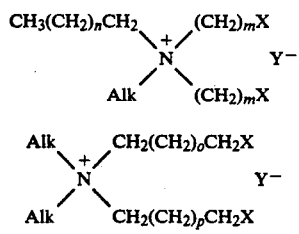

wherein:
X s bromine or chlorine or iodine
Y is an anion
Alk is an alkyl group containing from about 1 to about 4 carbon atoms
n is an integer with a value of from about 10 to about 22
m is an integer with a value of from about 1 to about 4
o is an integer with a value of from about 8 to about 11,
p is an integer with a value of from about 8 to about 11,
with the proviso that the total number of aliphatic carbon atoms in the cation is not more than about 28,
and further compounds in which one or both long chain alkyl groups is interrupted with a phenylene group so that the structure of the interrupted group can be represented by

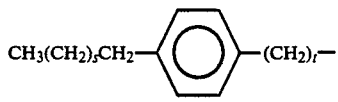

wherein s is an integer of from about 8 to about 17 and t is an integer from about 1 to about 5, and thereafter rinsing the hair with water.

4. A process for conditioning human hair which comprises treating the hair with an aqueous composition containing from about 0.1 to about 10% by weight of the total composition of at least one compound represented by the formulas:

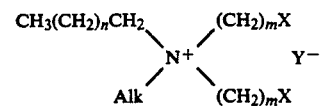

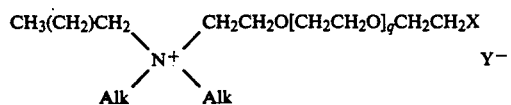

wherein:
X is bromine, chlorine or iodine
Y is an anion,
Alk is an alkyl group containing from about 1 to about 4 carbon atoms,
n is an integer with a value of from about 10 to about 22, and
m is an integer with a value of from about 1 to about 4 with the proviso that the total number of aliphatic carbon atoms in the cation is not greater than about 28, and
q is an integer with a value of from about 0 to about 20 and further compounds in which one or both long chain alkyl group is interrupted with a phenylene group so that the structure of the interrupted group can be represented by

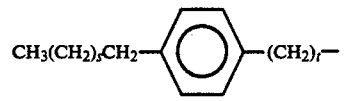

wherein s is an integer of from about 8 to about 17 and t is an integer from about 1 to about 5, and thereafter rinsing the hair with water.

5. The invention according to claim 1 or 7 wherein the composition contains a compound selected from the group of methyl-di-[2-bromoethyl)]-hexdecyl ammonium bromide; dimethyl-di[(11-bromoundecyl)] ammonium bromide; methyl-tridecyl-di[(2-bromoethyl)] ammonium chloride; ethyl-dodecyl-di[(2-bromoethyl)] ammonium bromide; n-butyl-tetradecyl-di[(2-chloroethyl)] ammonium bromide and ethyl-hexadecyl-di[(2-chloroethyl)] ammonium chloride.

6. The invention according to claim 2 or 4 wherein the composition contains a compound selected from the group dimethyl-(2-bromoethyl)-hexadecyl ammonium bromide; dimethyl-(2-bromoethyl)-4-(dodecyl)phenylmethylene ammonium bromide and dimethyl-hexadecyl-[2-(bromoethoxy)ethyl] ammonium bromide.

* * * * *